United States Patent
Whittaker et al.

(10) Patent No.: US 10,117,698 B2
(45) Date of Patent: Nov. 6, 2018

(54) DEVICES, SYSTEMS, AND METHODS FOR DRIVING AN ANCHOR INTO BONE

(71) Applicant: DePuy Synthes Products, Inc., Raynham, MA (US)

(72) Inventors: Gregory R. Whittaker, Stoneham, MA (US); Gary McAlister, Franklin, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 296 days.

(21) Appl. No.: 15/057,307

(22) Filed: Mar. 1, 2016

(65) Prior Publication Data

US 2017/0252086 A1    Sep. 7, 2017

(51) Int. Cl.
| | | |
|---|---|---|
| A61B 17/88 | (2006.01) | |
| A61B 17/84 | (2006.01) | |
| A61B 17/04 | (2006.01) | |
| A61F 2/08 | (2006.01) | |
| A61B 17/86 | (2006.01) | |

(52) U.S. Cl.
CPC ...... *A61B 17/8872* (2013.01); *A61B 17/0401* (2013.01); *A61B 17/844* (2013.01); *A61B 17/8685* (2013.01); *A61B 17/8875* (2013.01); *A61B 17/8897* (2013.01); *A61F 2/0805* (2013.01); *A61F 2002/0864* (2013.01)

(58) Field of Classification Search
CPC ............ A61B 17/8872; A61B 17/8645; A61B 17/844; A61B 17/8875; A61C 8/0033; A61C 2/0811; A61F 2002/0823
See application file for complete search history.

(56) References Cited

U.S. PATENT DOCUMENTS

| | | |
|---|---|---|
| 4,687,392 A | 8/1987 | Bidwell |
| 5,290,296 A | 3/1994 | Phillips |
| 5,290,297 A | 3/1994 | Phillips |
| 5,948,000 A | 9/1999 | Larsen et al. |
| 5,948,001 A | 9/1999 | Larsen |
| 6,554,862 B2 | 4/2003 | Hays et al. |
| 7,104,999 B2 | 9/2006 | Overaker |
| 7,309,355 B2 | 12/2007 | Donnelly et al. |
| 8,226,714 B2 | 7/2012 | Beck, Jr. et al. |
| 2002/0120275 A1 | 8/2002 | Schmieding et al. |
| 2004/0002709 A1 | 1/2004 | Gabriel et al. |
| 2004/0267361 A1 | 12/2004 | Donnelly et al. |

(Continued)

OTHER PUBLICATIONS

U.S. Appl. No. 14/610,602 entitled "Biceps Tenodesis Implants and Delivery Tools" filed Jan. 30, 2015.

(Continued)

*Primary Examiner* — Andrew Yang

(57) ABSTRACT

In general, devices, systems, and methods for driving an anchor into bone are provided. In one embodiment, a surgical tool is provided that includes a driver tool with a handle and an elongate shaft. A resistance element is disposed within the handle. An inner portion of an anchor is retained on a distal end of the elongate shaft, and a guidewire extends between the resistance element and an outer portion of the anchor that is in bone. As force is applied distally to the handle, the guidewire pushes the anchor into the bone before overcoming force of the resistance element and thereby allowing the inner portion of the anchor to be driven into the outer portion of the anchor.

19 Claims, 5 Drawing Sheets

(56) References Cited

U.S. PATENT DOCUMENTS

2008/0215060 A1   9/2008  Garcia et al.
2009/0275954 A1  11/2009  Phan et al.
2009/0287259 A1  11/2009  Trenhaile et al.
2013/0226192 A1*  8/2013  Nino ..................... B25B 13/466
                                                    606/104

OTHER PUBLICATIONS

European Search Report for Application No. 17158361.0 dated Aug. 16, 2017.

* cited by examiner

DEVICES, SYSTEMS, AND METHODS FOR DRIVING AN ANCHOR INTO BONE

FIELD

The present disclosure relates generally to devices, systems, and methods for driving an anchor into bone.

BACKGROUND

A variety of disorders can require anchoring a tendon to bone through a procedure such as a biceps tenodesis, for example rotator cuff tears, superior labrum anterior posterior tears, impingement syndrome, and capsular injuries. A traditional repair procedure involves drilling a bone hole into the associated bone and using a tendon fork to push the tendon down into the bone hole. An anchor is then delivered into the bone hole to anchor the tendon within the bone hole, which can involve delivering an outer sheath of the anchor into the bone hole to secure the tendon and then delivering an inner screw of the anchor to secure the anchor.

While traditional procedures can provide an effective means for anchoring a tendon to bone, they can suffer from any of one or more drawbacks. For example, traditional procedures require the use of numerous tools, which can lead to a prolonged procedure and/or increased costs. For another example, tension of the tendon can cause the tendon to experience a rebound effect and the anchor to be proud above a surface of the bone, thereby causing the tendon to push the anchor out of the bone hole and accordingly prolong healing, cause damage to adjacent body structures, and/or result in the anchor and/or the tendon mooring being entirely out of the bone.

Accordingly, there remains a need for improved devices, systems, and methods for driving an anchor into bone.

SUMMARY

In general, devices, systems, and methods for driving an anchor into bone are provided.

In one aspect, a surgical tool is provided that in one embodiment includes a driver tool configured to drive an anchor into a bone. The driver tool includes a handle and an elongate shaft extending distally from the handle. The elongate shaft has an inner passageway extending therethrough, and the handle has an inner cavity formed therein. The inner passageway is in communication with the inner cavity. The surgical tool also includes a resistance element that is disposed within the inner cavity. A force required to cause the resistance member to yield is greater than a force required to drive the anchor into the bone. The surgical tool also includes an anchor component retainer that is formed on a distal end of the elongate shaft.

The surgical tool can vary in any number of ways. For example, the resistance element can include a material that is softer than a material surrounding the inner cavity. For another example, the material disposed in the inner cavity can be semi-rigid material, and material surrounding the inner cavity can be rigid material. For yet another example, the resistance member yielding can include penetration thereof by a guidewire extending through the inner passageway. For still another example, the resistance member yielding can include compression thereof by a guidewire extending through the inner passageway. For another example, the resistance element can include a spring.

In another aspect, a surgical kit is provided that in one embodiment includes a driver tool and a guidewire. The driver tool includes a handle and an elongate shaft extending distally from the handle. The handle has a resistance element disposed therein. The guidewire has a proximal end disposed within the handle, and a length of the guidewire extends through an inner passageway of the elongate shaft. The driver tool is configured to drive an anchor into bone, thereby causing the proximal end of the guidewire to move proximally within the handle after the guidewire overcomes a bias force exerted on the guidewire by the resistance element.

The surgical kit can vary in any number of ways. For example, the resistance element can include an inner portion of semi-rigid material within the handle into which the proximal end of the guidewire can be configured to move proximally within the handle. For another example, the resistance element can include a bias element disposed in the handle and applying the distal bias force to the guidewire, the distal bias force being configured to be overcome by the driver tool driving the anchor into bone to allow the proximal movement of the proximal end of the guidewire within the handle.

For yet another example, the surgical kit can include an anchor including an outer member and an inner member. The inner member can be configured to be removably disposed on a distal end of the elongate shaft, and the outer member can be configured to have a distal end of the guidewire disposed therein. The driver tool can be configured to drive the anchor into bone and thereby cause the guidewire to move distally and thereby push the outer member distally to move the outer member distally relative to the bone. The outer member can be configured to move distally within the bone before the proximal end of the guidewire moves proximally within the handle, the driver tool can be configured to drive the anchor into bone to cause the inner member to move into the outer member after the driver tool causes the distal movement of the outer member, and/or the inner member can be configured to be removably disposed on the distal end of the elongate shaft at a location that is entirely proximal to the outer member having the distal end of the guidewire disposed therein.

In another aspect, a surgical method is provided that in one embodiment includes disposing a tendon in a bone hole, and disposing an outer member of an anchor in the bone hole. The method also includes distally advancing a driver tool having an inner member of the anchor disposed on a distal end thereof, thereby causing a guidewire disposed in an inner passageway of the driver tool to push the outer member in a distal direction within the bone hole, then causing the guidewire overcome a bias force applied thereto by a resistance element disposed in the driver tool and to move proximally within the inner passageway, and then causing the inner member to be disposed within the outer member to secure the tendon within the bone hole.

The method can have any number of variations. For example, the guidewire moving proximally within the inner passageway can include a proximal end of the guidewire moving into an inner cavity formed in a proximal handle of the driver tool. In at least some embodiments, the resistance element can be disposed within the inner cavity and can include a material that is softer than a material surrounding the inner cavity, and the proximal movement of the guidewire can result in the guidewire moving proximally within the softer material. In at least some embodiments, the resistance element can be disposed within the inner cavity and can include a spring disposed therein that provides the bias force, the bias force can bias the guidewire in a distal direction, and the distal advancement of the driver tool can overcome the bias force to allow the proximal movement of the guidewire.

For another example, the distal advancement of the driver tool can cause the guidewire to penetrate into the resistance element disposed within the driver tool. For yet another example, prior to the distal advancement of the driver tool, a distal end of the guidewire can be disposed within the outer member and the inner member can be disposed on the distal end of the driver tool at a location that is entirely proximal to the outer member having the distal end of the guidewire disposed therein.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Figure 1:
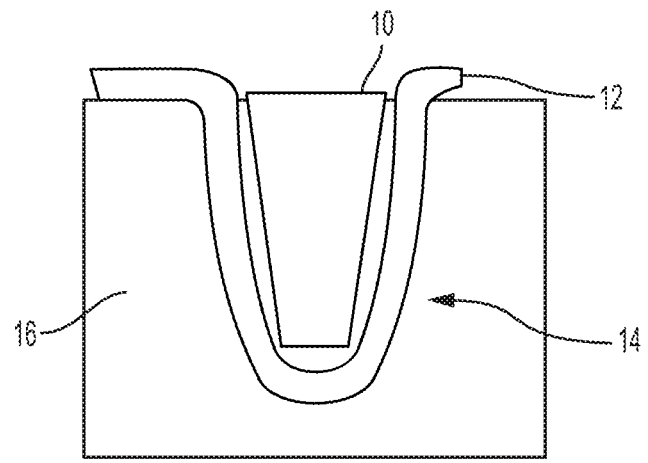
FIG. 1 is a partial cross-sectional side view of one embodiment of an anchor and a tendon disposed in a bone hole.
Figure 2:
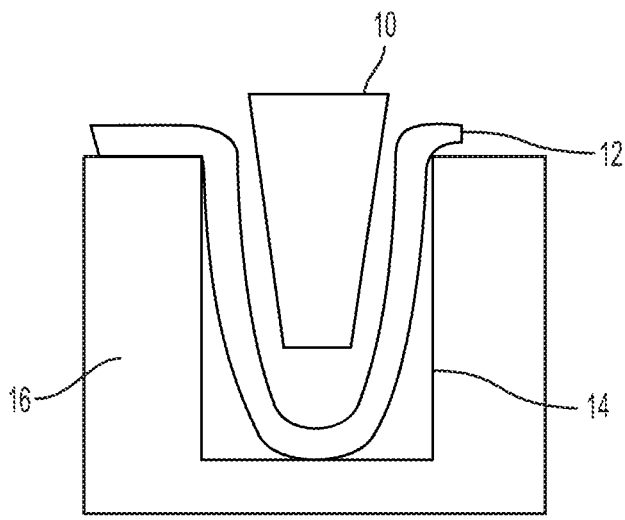
FIG. 2 is a partial cross-sectional side view of the anchor of FIG. 1 being pushed out of the bone hole by the tendon.

As illustrated in FIG. 1, an anchor 10 and a tendon 12 can be disposed in a bone hole 14 to secure the tendon 12 to bone 16. However, tension of the tendon 12 can cause the tendon 12 to experience a rebound effect and the anchor 10 to be proud above a surface of the bone 16, as illustrated in FIG. 2. As discussed further below, a driver tool used to drive an anchor such as the anchor 10 into a bone such as the bone 16 can be configured to help reduce the chances of the rebound effect occurring and the anchor being proud, if not entirely eliminate the chances.

Various exemplary devices, systems, and methods for driving an anchor into bone are provided. In general, a driver tool can be configured to drive an anchor into a bone. The driver tool can have a handle and an elongate shaft that extends from the handle. The elongate shaft can have an inner passageway extending therethrough and can have an anchor component retainer formed on a distal end thereof. The handle can have an inner cavity formed therein in communication with the inner lumen. A resistance element can be disposed in the inner cavity, and an inner portion of the anchor can be disposed on the anchor component retainer. A guidewire can extend through the inner passageway and have a proximal end in contact with the resistance element. A distal end of the guidewire can terminate in an outer portion of the anchor.

In response to a user applying force to the handle, the distal end of the guidewire can push the anchor into bone, and the proximal end of the guidewire can be forced against the resistance element. As force by the user increases on the handle, the guidewire can overcome a bias of the resistance element disposed in the handle and thus cause the resistance element to yield. As the driver tool drives an inner portion of the anchor distally into the outer portion of the anchor already in the bone, the guidewire can help keep the outer portion secured and flush in the bone until the guidewire overcomes the bias of the resistance element, thereby causing the resistance element to yield, such that the driver tool is able to drive the inner portion of the anchor into place within the outer portion of the anchor. A force required to cause the resistance member to yield can thus be greater than a force required to drive the anchor into the bone, and the driver tool can consequently provide proper seating of the anchor in bone while reducing chances of the rebound effect and the anchor being proud above a surface of the bone. The rebound effect may be reduced, if not eliminated, and the anchor may be less likely to be, if not be prevented from being, proud in a manner transparent to the user and without any particular action being taken by the user other than the familiar action of applying force to a driver tool to drive an anchor. The user thus need not have any special training to effectively use the driver tool because the rebound effect reduction and the anchor being prevented from being proud can occur automatically in the course of using the driver tool to drive the anchor into the bone.

Figure 3:
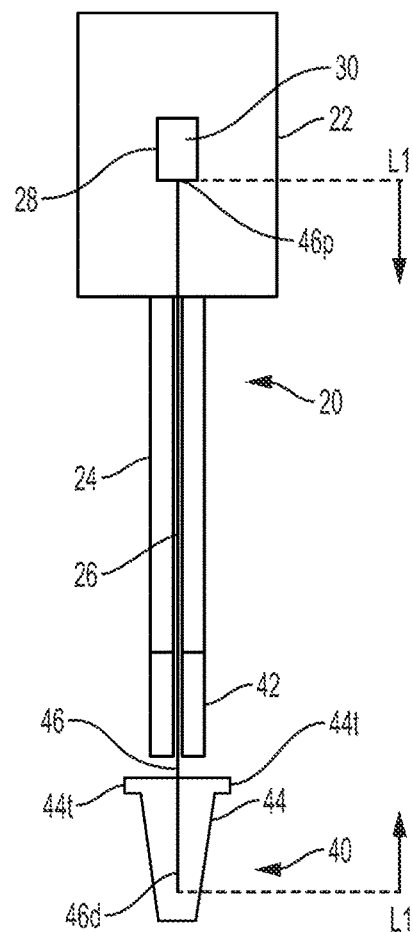
FIG. 3 is a cross-sectional side view of one embodiment of a driver tool coupled to one embodiment of an anchor and one embodiment of a guidewire.

FIG. 3 illustrates one embodiment of a driver tool 20 coupled to one embodiment of a guidewire 46 and one embodiment of an anchor 40. The driver tool 20 has a handle 22 and an elongate shaft 24 extending distally from the handle 22. An inner passageway 26 extends through the elongate shaft 24, and the handle 22 has an inner cavity 28 formed therein. The inner passageway 26 communicates with the inner cavity 28. The inner cavity 28 of the handle 22 has a resistance element 30 disposed therein. The resistance element 30 in the embodiment in FIG. 3 is a semi-rigid material (e.g., silicone, urethane, etc.) that is configured such that a force required to cause the resistance member 30 to yield is greater than a force required to drive the anchor 40 into bone (not shown), as discussed further below. The resistance element can include a material that is softer than a material surrounding the inner cavity 28 and/or material disposed in the inner cavity 28 can be semi-rigid material while material of the handle 22 surrounding the inner cavity 28 can be rigid material, e.g., stainless steel, polyether ether ketone (PEEK), polycarbonate, etc.

An anchor component retainer (obscured in FIG. 3) is formed on a distal end of the elongate shaft 24 and is configured to releasably retain an inner portion 42 of the anchor 40 on the distal end of the elongate shaft 24. The anchor component retainer can have a variety of configurations, such as threads configured to mate to corresponding threads of the inner portion 42.

The handle 22 and the elongate shaft 24 of the driver tool 20 have cylindrical shapes in this illustrated embodiment, but the handle 22 and the elongate shaft 24 can have a variety of sizes, shapes, and configurations. In general, the handle 22 is configured to be held in a hand of a user and to have a distal force applied thereto by the user (or another user, such as an assistant). In other embodiments, for example, the handle and/or the elongate shaft can have another shape, such as the handle having a spherical shape, an elliptical shape, a cone shape, a triangular prism shape, etc., and the elongate shaft having a triangular prism shape, a rectangular prism shape, etc. The handle 22 is fixed to the elongate shaft 24 in this illustrated embodiment, but the handle can be detachable from the elongate shaft in at least some embodiments. The elongate shaft being detachable from the handle can allow the elongate shaft to be reusable while the handle can be disposable so that a new resistance element can be used.

As illustrated in FIG. 3, the guidewire 46 can be coupled to the driver tool 20 to extend distally from the resistance element 30 to an outer portion 44 of the anchor 40. A distal end 46d of the guidewire 46 is configured to contact an inner bottom surface of the outer portion 44 of the anchor 40, and a proximal end 46p of the guidewire 46 is configured to contact the resistance element 30. The guidewire 46 is configured to move proximally into the inner cavity 28 and counteract the force of the resistance member 30 when the driver tool 20 is driving the inner portion 42 of the anchor 40 into the outer portion 44 of the anchor 40, as discussed further below. The guidewire 46 has a length L1 that is long enough so that the proximal end 46p of the guidewire 46 contacts the resistance element 30 just before the inner portion 42 of the anchor 40 contacts the outer portion 44 of the anchor 40 when the tool 20 is in use so that the distal end 46d of the guidewire 46 can facilitate distal positioning of the outer portion 44 of the anchor 40 within bone.

The handle 22, the shaft 24, and the guidewire 46 can each have a variety of sizes. In an exemplary embodiment, the handle 22 can have a length in a range of about 5 to 10 cm and a diameter in a range of about 1 to 3 cm, the shaft 24 can have a length in a range of about 10 to 30 cm (e.g., about 18 cm) and a diameter in a range of about 2 to 8 mm (e.g., about 5 mm), and the guidewire 46 can have a length in a range of about 10 to 30 mm and a diameter in a range of about 0.75 mm to 3 mm (e.g., about 1 mm). A length of the guidewire 46 will typically be chosen taking into consideration a length of the shaft 24 and a size of the anchor 40 with which the guidewire 46 will be used so that the guidewire 46 can be relatively positioned with respect to the shaft 24 and the anchor 40 and operatively used as described herein.

As mentioned above, the anchor 40 includes the inner portion 42 and the outer portion 44. The outer portion 44 of the anchor 40 has tabs 44t configured to engage a surface of bone as the outer portion 44 is forced into the bone. The inner portion 42 of the anchor 40 is configured to be inserted into the outer portion 44 of the anchor 40 to cause the outer portion 44 to expand and thereby secure the anchor 40 in the bone. The anchor 40 can have any of a variety of sizes, such as 23 mm. Various embodiments of anchors including inner and outer portions are described in further detail in U.S. Pat. No. 6,554,862 entitled "Graft ligament anchor and method for attaching a graft ligament to a bone" issued on Apr. 29, 2003, U.S. Pat. No. 7,309,355 entitled "Flexible tibial sheath" issued on Dec. 18, 2007, and U.S. Pat. No. 8,226, 714 entitled "Femoral fixation" issued on Jul. 24, 2012, which are hereby incorporated by reference in their entireties.

As distal force is applied to the handle 22 by a user, the resistance element 30 of the driver tool 20 acts to apply a distal force to the proximal end 46p of the guidewire 46, while the distal end 46d of the guidewire 46 applies a distal force against the outer portion 44 of the anchor 40 to keep the outer portion 44 pushed in a distal direction into a bone hole in bone. As the driver tool 20 drives the anchor 40 distally into the bone, the resistance element 30 is penetrated by the guidewire 46 as the inner portion 42 of the anchor 40 on the anchor component retainer 32 of the driver tool 20 is driven into the outer portion 44 of the anchor 40.

A first force is required to be applied to the guidewire 46 for the guidewire 46 to push the outer portion 44 of the anchor 40 distally in bone, while a second, greater force is required to cause the guidewire 46 to penetrate the resistance element 30. In other words, the second force required for the guidewire 46 to overcome a bias of the resistance element 30 is greater than the first force required for the guidewire 46 to urge the outer portion 44 of the anchor 40 into bone. The outer portion 44 of the anchor 40 may thus be pushed as distally far as possible into the bone by the guidewire 46 before the inner portion 42 of the anchor 40 is advanced into the outer portion 44, which can only occur after the guidewire 46 has overcome the bias force of the resistance element 30. The anchor 40, the guidewire 46, and the elongate shaft 24 can all have known lengths so it can be known when the guidewire 46 will contact and then overcome the bias of the resistance element 30. Examples of first and second force pairs are a first force of about 1 pound and a second force of about 3 pounds, and a first force of about 2 pounds and a second force of about 5 pounds, although other forces can be used.

Figure 4:
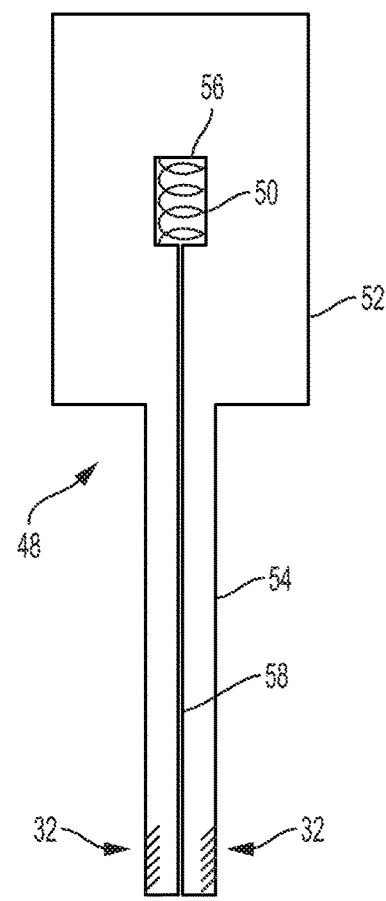
FIG. 4 is a cross-sectional side view of another embodiment of a driver tool.

While the resistance element 30 illustrated in FIG. 3 is a plug of semi-rigid material that fills the inner cavity 28, the resistance element 30 can have other forms. For example, a resistance element 50 including a coil spring is illustrated in FIG. 4 embedded in a handle 52 of a driver tool 48. The driver tool 48 can generally be configured and used similar to the tool 20 of FIG. 3, e.g., include the handle 52, an elongate shaft 54 extending distally from the handle 52, an inner lumen 58 extending through the shaft 54, an inner cavity 56 within the handle 52, and an anchor component retainer 32, which is in the form of a thread in this illustrated embodiment. A guidewire coupled to the driver tool 48 and extending through the lumen 58, similar to the guidewire 46 extending through the lumen 26, would not penetrate the resistance element 50 in response to overcoming a bias force provided thereby but would instead compress the resistance element 50, e.g., compress the spring. The resistance element 50 is a coil spring configured to be compressed in this illustrative embodiment, but other types of compressible members can be used, such as another type of spring (e.g., a leaf spring, a rubber band, etc.)

A kit can be provided including any two or more of a driver tool, a guidewire, and an anchor. For example in some embodiments, a guidewire can be pre-extended through a driver tool and be provided together as a kit that can also include one or more anchors or that can be used with an anchor separately obtained.

The driver tools described herein can be used to drive an anchor into bone and can be used in any of a variety of surgical procedures where a tendon is attached to a bone hole using an anchor, such as when a biceps tendon is tenodesed using an anchor such as a Milagro® interference screw available from DePuy Mitek of Raynham, Mass. FIGS. 5-10 illustrate one embodiment of such a method using the tool 20, the guidewire 46, and the anchor 40 of FIG. 3, though other embodiments of tools, guidewires, and anchors described herein can be similarly used. While the anchor 40 is used to secure a tendon, a tendon is not shown in FIGS. 5-10 for clarity of illustration.

Figures 5, 6:
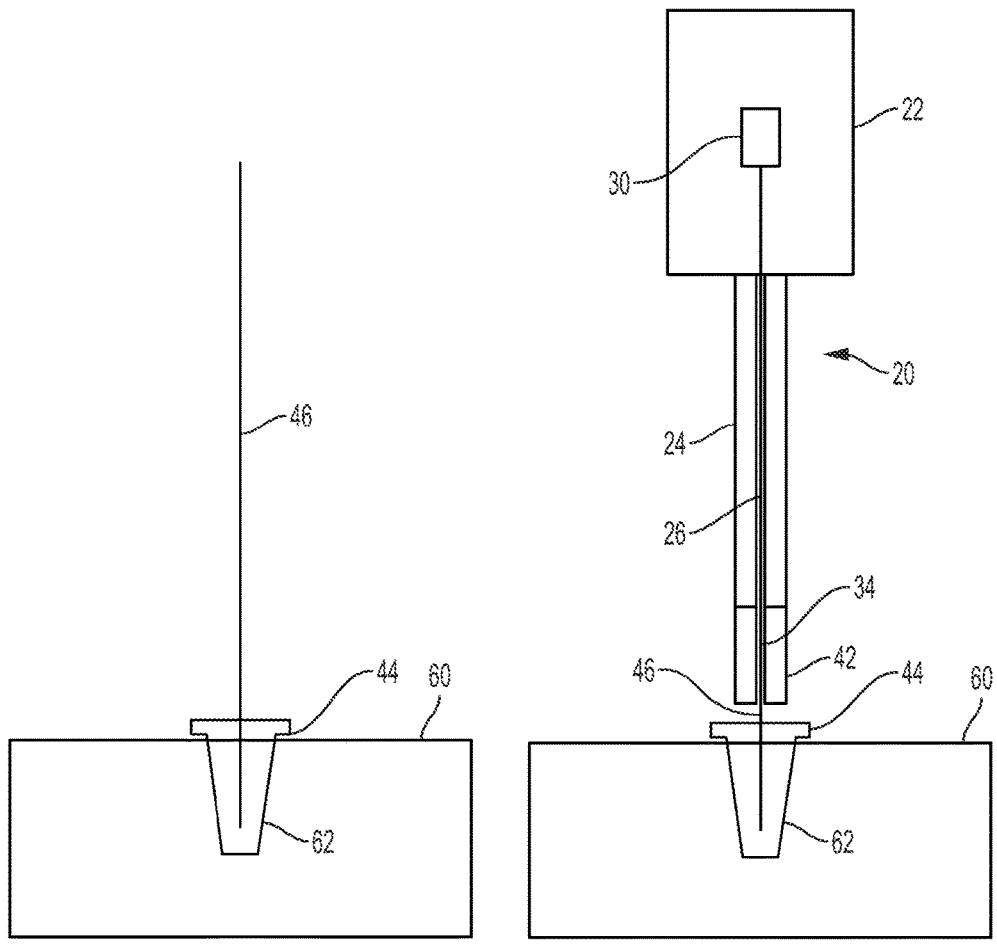
FIG. 5 is a cross-sectional side view of an outer portion of the anchor of FIG. 3 and the guidewire of FIG. 3 disposed in a bone hole.
FIG. 6 is a cross-sectional side view of the anchor and the guidewire of FIG. 5 with the driver tool of FIG. 3 and an inner portion of the anchor of FIG. 3 coupled to the guidewire.

A user can dispose a tendon in a bone hole 62 through any of a variety of methods, for example by using a method described in U.S. patent application Ser. No. 14/610,602 entitled "Biceps Tenodesis Implants and Delivery Tools" filed on Jan. 30, 2015, which is incorporated by reference herein in its entirety. The tendon (not shown) can be held temporarily in place by disposing the outer portion 44 of the anchor 40 in the bone hole 62 formed in bone 60, as illustrated in FIG. 5. As will be appreciated by a person skilled in the art, the bone hole 62 can be pre-formed in the bone 60 prior to the tendon and/or the outer portion 44 being disposed therein. The outer portion 44 of the anchor 40 has the guidewire 46 extending therefrom. The guidewire 46 extends from the outer portion 44 while the outer portion 44 is being driven into the bone hole 62, but in other embodiments the guidewire 46 can be inserted into the outer portion 44 after the outer portion 44 has been driven into the bone 60.

Figure 7:
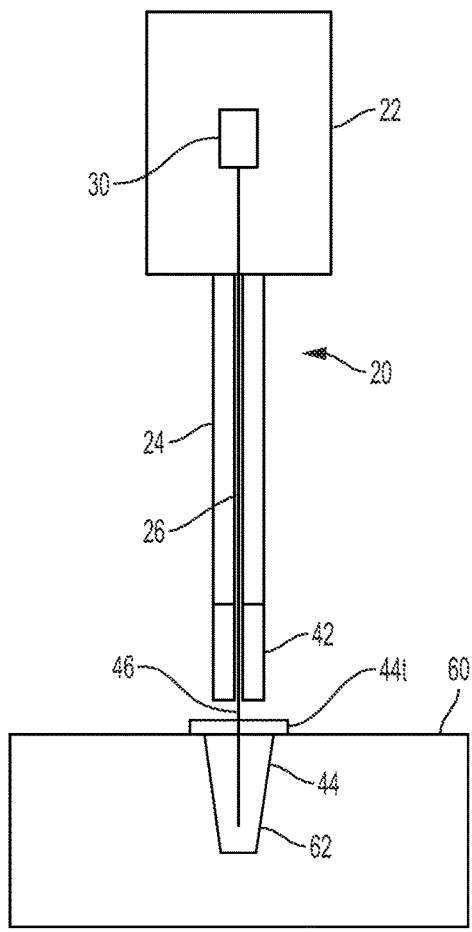
FIG. 7 is a cross-sectional side view of the driver tool of FIG. 6 having distally advanced the outer portion of the anchor into the bone hole.

The driver tool 20 having the inner portion 42 coupled to the anchor component retainer is advanced in a distal direction over the guidewire 46 such that the guidewire 46 is disposed in the inner passageway 26 of the driver tool 20 and in an inner passageway 34 of the inner portion 42, as shown in FIG. 6. A user then applies a distal force to the handle 22 to distally advance the driver tool 20 with the inner portion 42 of the anchor 40 disposed thereon relative to the outer portion 44. The user can apply a force directly to the handle 22 by hand, indirectly through another tool (e.g., a mallet, etc.), or indirectly through the user's control of the tool 20 via a robotic surgical system. The distal force applied to the tool 20 causes the guidewire 46 to push the outer portion 44 of the anchor 40 in a distal direction within the bone hole 62 and thus also press the tendon against the bone 60 within the bone hole 62. The tabs 44t of the outer portion 44 can act as a stop by engaging a surface of the bone 60 to stop distal movement of the outer portion 44 at a certain point, as illustrated in FIG. 7.

Figure 8:
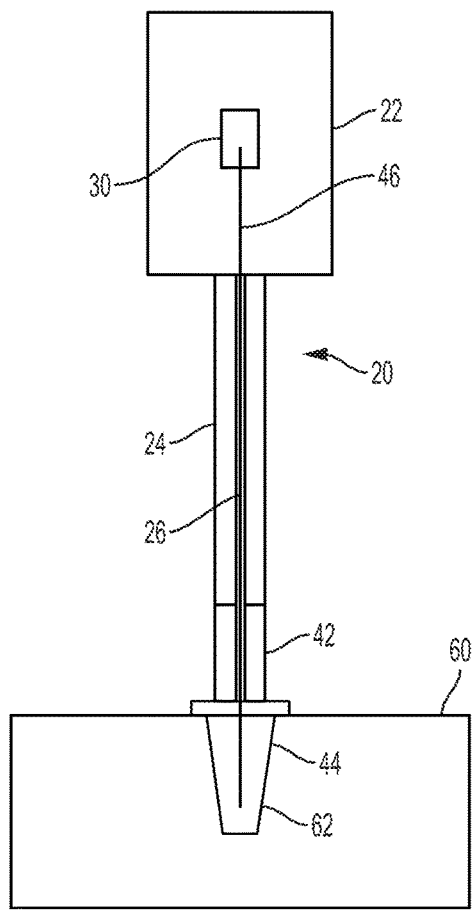
FIG. 8 is a cross-sectional side view of the driver tool of FIG. 7 with a proximal end of the guidewire advanced into a cavity of the driver tool.
Figure 9:
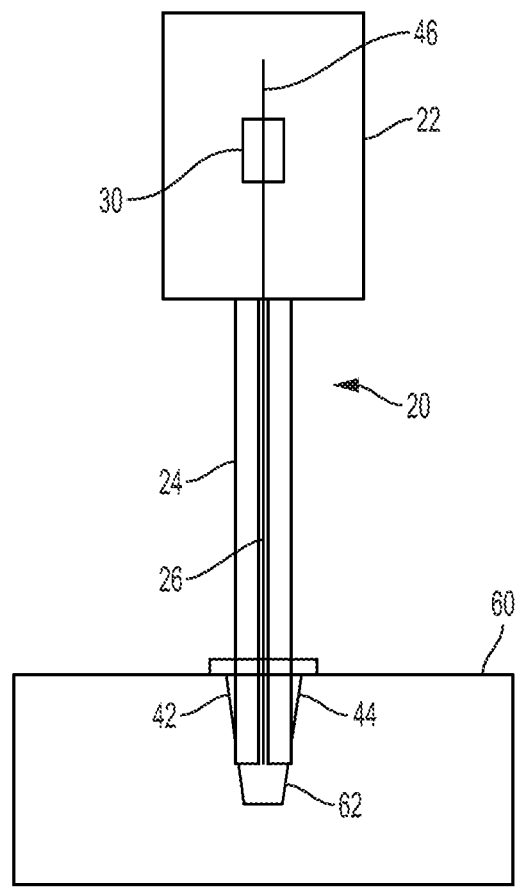
FIG. 9 is a cross-sectional side view of the driver tool of FIG. 8 having driven the inner portion of the anchor into the outer portion of the anchor.
Figure 10:
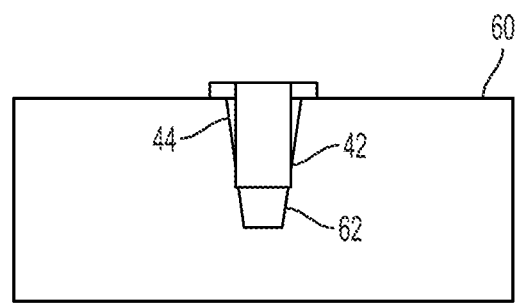
FIG. 10 is a cross-sectional side view of the inner and outer portions of the anchor of FIG. 9 disposed in the bone hole.

As the user continues to apply distal force to the handle 22, the force eventually causes the guidewire 46 to overcome biasing of the resistance element 30 after the distal pushing of the outer portion 44, which causes the guidewire 46 to move proximally within the inner passageway 26 and to move into the inner cavity 28 and penetrate the resistance element 30, as illustrated in FIG. 8. The inner portion 42 of the anchor 40 is then able to advance distally into the outer portion 44 of the anchor 40 as the inner portion 42 slides distally along the guidewire 46. As the guidewire 46 continues to move proximally and the inner portion 42 continues to move distally, the inner portion 42 becomes disposed within the outer portion 44 of the anchor 40, as illustrated in FIG. 9. The tendon is thereby secured in the bone hole 62 with the anchor 40 fully driven into the bone 60. The driver tool 20 and the guidewire 46 are then removed by being pulled away proximally, leaving the anchor 40 secured and flush in the bone 60 and leaving the tendon secured in the bone 60 by the anchor 40, as shown in FIG. 10.

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
   a driver tool configured to drive an anchor into a bone, the driver tool including a handle and an elongate shaft extending distally from the handle, the elongate shaft having an inner passageway extending therethrough, the handle having an inner cavity formed therein, the inner passageway being in communication with the inner cavity;
   a resistance element disposed within the inner cavity, a force required to cause the resistance member to yield being greater than a force required to drive the anchor into the bone; and
   an anchor component retainer formed on a distal end of the elongate shaft
   wherein the resistance member yielding includes penetration thereof by a guidewire extending through the inner passageway.

2. The surgical tool of claim 1, wherein the resistance element includes a material that is softer than a material surrounding the inner cavity.

3. The surgical tool of claim 2, wherein the material disposed in the inner cavity is semi-rigid material, and material surrounding the inner cavity is rigid material.

4. A surgical kit, comprising:
   a driver tool including a handle and an elongate shaft extending distally from the handle, the handle having a resistance element disposed therein; and
   a guidewire having a proximal end disposed within the handle, and a length of the guidewire extending through an inner passageway of the elongate shaft;
   wherein the driver tool is configured to drive an anchor into bone, thereby causing the proximal end of the guidewire to move proximally within the handle after the guidewire overcomes a distal bias force exerted on the guidewire by the resistance element.

5. The kit of claim 4, wherein the resistance element includes an inner portion of semi-rigid material within the handle into which the proximal end of the guidewire is configured to move proximally within the handle.

6. The kit of claim 4, wherein the resistance element includes a bias element disposed in the handle and applying the distal bias force to the guidewire, the distal bias force being configured to be overcome by the driver tool driving the anchor into bone to allow the proximal movement of the proximal end of the guidewire within the handle.

7. The kit of claim 4, further comprising an anchor including an outer member and an inner member, the inner member being configured to be removably disposed on a distal end of the elongate shaft, and the outer member being configured to have a distal end of the guidewire disposed therein.

8. The kit of claim 7, wherein the driver tool is configured to drive the anchor into bone and thereby cause the guidewire to move distally and thereby push the outer member distally to move the outer member distally relative to the bone.

9. The kit of claim 8, wherein the outer member is configured to move distally within the bone before the proximal end of the guidewire moves proximally within the handle.

10. The kit of claim 8, wherein the driver tool is configured to drive the anchor into bone to cause the inner member to move into the outer member after the driver tool causes the distal movement of the outer member.

11. The kit of claim 7, wherein the inner member is configured to be removably disposed on the distal end of the elongate shaft at a location that is entirely proximal to the outer member having the distal end of the guidewire disposed therein.

12. A surgical method, comprising:
  disposing a tendon in a bone hole;
  disposing an outer member of an anchor in the bone hole; and
  distally advancing a driver tool having an inner member of the anchor disposed on a distal end thereof, thereby causing a guidewire disposed in an inner passageway of the driver tool to push the outer member in a distal direction within the bone hole, then causing the guidewire to overcome a bias force applied thereto by a resistance element disposed in the driver tool and move proximally within the inner passageway, and then causing the inner member to be disposed within the outer member to secure the tendon within the bone hole.

13. The method of claim 12, wherein the guidewire moving proximally within the inner passageway includes a proximal end of the guidewire moving into an inner cavity formed in a proximal handle of the driver tool.

14. The method of claim 13, wherein the resistance element is disposed within the inner cavity and includes a material that is softer than a material surrounding the inner cavity, the proximal movement of the guidewire resulting in the guidewire moving proximally within the softer material.

15. The method of claim 13, wherein the resistance element is disposed within the inner cavity and includes a spring disposed therein that provides the bias force, the bias force biasing the guidewire in a distal direction, and the distal advancement of the driver tool overcoming the bias force to allow the proximal movement of the guidewire.

16. The method of claim 12, wherein the distal advancement of the driver tool causes the guidewire to penetrate into the resistance element disposed within the driver tool.

17. The method of claim 12, wherein, prior to the distal advancement of the driver tool, a distal end of the guidewire is disposed within the outer member and the inner member is disposed on the distal end of the driver tool at a location that is entirely proximal to the outer member having the distal end of the guidewire disposed therein.

18. A surgical tool, comprising:
  a driver tool configured to drive an anchor into a bone, the driver tool including a handle and an elongate shaft extending distally from the handle, the elongate shaft having an inner passageway extending therethrough, the handle having an inner cavity formed therein, the inner passageway being in communication with the inner cavity;
  a resistance element disposed within the inner cavity, a force required to cause the resistance member to yield being greater than a force required to drive the anchor into the bone; and
  an anchor component retainer formed on a distal end of the elongate shaft
  wherein the resistance member yielding includes compression thereof by a guidewire extending through the inner passageway.

19. The surgical tool of claim 18, wherein the resistance element includes a spring.

* * * * *